United States Patent [19]

Schneider et al.

[11] Patent Number: 4,708,023
[45] Date of Patent: Nov. 24, 1987

[54] SAMPLE HANDLING APPARATUS

[75] Inventors: Ortwin Schneider, Weiterstadt; Nikolaos Georgitsis, Heusenstamm, both of Fed. Rep. of Germany

[73] Assignee: Erweka Apparatebau GmbH, Heusenstamm, Fed. Rep. of Germany

[21] Appl. No.: 870,967

[22] Filed: Jun. 5, 1986

[30] Foreign Application Priority Data

Jun. 7, 1985 [DE] Fed. Rep. of Germany ....... 3520438

[51] Int. Cl.[4] .......................... G01N 1/14; G01N 35/00
[52] U.S. Cl. .............................. 73/863.31; 73/863.33; 73/863.02; 422/81
[58] Field of Search ........... 73/863.31, 863.32, 863.33, 73/863.02, 863.03, 864.11, 864.12, 864.15, 864.21, 864.22, 864.24, 864.31, 864.34, 864.73, 864.25, 864.35, 864.74; 422/81, 82; 436/179

[56] References Cited

U.S. PATENT DOCUMENTS

| | | | |
|---|---|---|---|
| 3,776,700 | 12/1973 | Gallant | 73/863.32 X |
| 3,846,075 | 11/1974 | Cioffi | 73/863.33 X |
| 4,108,602 | 8/1978 | Hanson et al. | 422/81 X |
| 4,228,831 | 10/1980 | Kerns | 73/864.12 |
| 4,286,637 | 9/1981 | Wilson | 73/864.24 X |
| 4,554,839 | 11/1985 | Hewett et al. | 73/863.32 X |

*Primary Examiner*—Tom Noland
*Attorney, Agent, or Firm*—Birch, Stewart, Kolasch & Birch

[57] ABSTRACT

A sample handling apparatus comprises probes for taking liquid samples from reaction vessels, pipes connected to the probes by lines and adapted for releasing the liquid samples into test tubes arranged below the pipes and for taking-in replenishing liquid from a storage trough, and a pump for transporting the liquid samples from the probes to the test tubes and for feeding replenishing liquid from the pipes to the reaction vessels. In the sample handling apparatus the lines are completely rinsed with replenishing liquid between taking samples. The sample handling apparatus may also be adapted for diluting the liquid samples in the test tubes and for feeding the diluted liquid samples to a measuring unit.

12 Claims, 4 Drawing Figures

SAMPLE HANDLING APPARATUS

BACKGROUND OF THE INVENTION

The invention relates to a sample handling apparatus designed at least for taking specimens or samples from reaction vessels and for providing a backfeed to the reaction vessels of the same amount of replenishing liquid as the amount (volume) of specimen taken.

Such sample collecting apparatuses are used in the pharmaceutical industry for taking samples or solutions of pharmaceutical products the long-term behaviour of which at body temperature (37° C.) is to be measured. When carrying out such measurements it is important that one measurement is not influenced by the preceding measurement, i.e. that the lines through which the samples to be measured flow have to be cleaned between the individual operations of taking samples. Furthermore, it has to be guaranteed that exactly the same amount of replenishing liquid is fed back to the reaction vessels, as has been taken for a previous sample. For this purpose in previous sample collecting apparatuses replenishing liquid is fed to the reaction vessels through the same pump which also is used for taking the samples. For introducing the replenishing liquid into the pump circulation it is necessary to provide a valve to realize the lines through which the samples flow from the reaction vessels to the test tubes and the line work through which the replenishing liquid flows from the storage vessel to the reaction vessels. The previous sample collecting apparatus has the disadvantage that the lines for the samples are not entirely rinsed by the replenishing liquid, because the lines for the replenishing liquid from the storage vessel to the valve are separate from the lines from the valve to the test tubes. Between the valves and the reaction vessels the liquid samples pass through the same lines as the replenishing liquid, of course the two liquids flowing in opposite directions.

SUMMARY OF THE INVENTION

It is a main object of the present invention to provide for a sample handling apparatus in which the entire sample collecting lines are rinsed by replenishing liquid between taking of samples, and which apparatus is adapted to be constructed for performing additional functions like diluting the liquid samples and feeding the diluted liquid samples to a measuring unit with low additional construction effort.

The sample handling apparatus according to this invention comprises:

a sample unit having a plurality of probes for taking liquid samples from a corresponding plurality of reaction vessels of a reaction unit, a sample collecting unit having a plurality of pipes for releasing the liquid samples into test tubes arranged in said sample collecting unit below said pipes, as well as for taking-in replenishing liquid and, for this purpose, being adapted to be immersed into replenishing liquid in a first storage means also arranged in said sample collecting unit, lines connecting said probes with said pipes, a transport means connected to said lines for transporting the liquid samples from said probes to said test tubes and for transporting the replenishing liquid from said first storage means to said reaction vessels, and a control means for controlling at least the operation of the sampling unit, the sample collecting unit and the transport means.

Since the pipes serve not only to release the samples into the test tubes but also to take in the replenishing liquid to refill the reaction vessels through the lines and the probes, the entire lines conducting the samples are rinsed with replenishing liquid between two operations of taking samples.

A further improved embodiment of the invention is a sample handling apparatus wherein said sample collecting unit comprises a first moving means for moving said pipes in an upward and downward direction to a first position in which they are located above said first storage means and to a second position in which they are immersed in a replenishing liquid in said first storage means, and wherein said sample collecting unit furthermore comprises a second moving means for moving said first storage means in a space between said test tubes and said pipes to a position below said pipes and to a position to the side of said pipes. In this embodiment only means for moving the pipes up and down and means for displacing the storage means have to be additionally provided in order to feed the liquid samples from the reaction vessels to the test tubes and to feed the replenishing liquid from the corresponding storage means to the reaction vessels.

A further improved embodiment of the invention is a sample handling apparatus comprising a second storage means arranged in the sample collecting unit and adapted to contain a diluted liquid, a valve means arranged in said lines in a position between said transport means and said probes and having three valves actuatable to allow liquid flow (a) between said probes and said pipes, (b) between said pipes and a measuring unit connected to one of said valves, and (c) between said pipes and a container unit connected to another one of said valves, where said pipes are also adapted to be immersed into the dilution liquid contained in said test tubes, and where said control means is adapted to control also the operation of said valve means. With this apparatus the additional functions of diluting the test samples in the test tubes and feeding the diluted test samples to a measuring unit are achieved at low additional construction effort.

A further improved embodiment of the invention is a sample handling apparatus wherein said sample collecting unit comprises a first moving means for moving said pipes in an upward and downward direction to a first position in which they are located above said first and second storage means, to a second position in which they are immersed in a replenishing liquid in said first storage means or in a dilution liquid in said second storage means, and to a third position in which they are immersed in the liquid contained in the test tubes, and wherein said sample collecting unit furthermore comprises a second moving means for moving said first and second storage means in a space between said test tubes and said pipes into a position below said pipes and to positions to said side of said pipes. In this embodiment the construction effort for providing the additional functions of diluting the test samples and feeding the diluted test samples to the measuring unit is very low, since the moving means for moving the pipes and the storage means can be simple in construction and easily controlled to bring the pipes and the storage means into the different operating positions.

A further improved embodiment of the invention is a sample handling apparatus wherein said first and second storage means comprise a first storage trough and a second storage trough connected to a first storage vessel and a second storage vessel, respectively, and wherein level control means are provided for refilling said first storage trough with replenishing liquid from said first storage vessel and for refilling said second storage trough with a dilution liquid from said second storage vessel to keep the liquid levels in said first and second storage troughs within predetermined limits. This embodiment has the advantage that the space needed for the storage troughs between the pipes and the test tubes can be kept narrow and that the storage troughs nevertheless always contain enough liquid for being functional.

A further improved embodiment of the invention is a sample handling apparatus wherein said first storage vessel and said second storage vessel are closed vessels and are mounted above said first storage trough or said second storage trough, respectively, and wherein said level control means comprise two first conduits and two second conduits, first ends of which first and second conduits are connected to the bottom of said first or second storage vessel and second ends of which first or second conduits extend into said first or second storage trough, respectively, to different depths whereby the liquids in said first and second storage troughs are kept within predetermined limits. By this arrangement the storage troughs are refilled automatically.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention, and wherein.

DETAILED DESCRIPTION OF PREFERRED EMBODIMENTS

Figure 1:
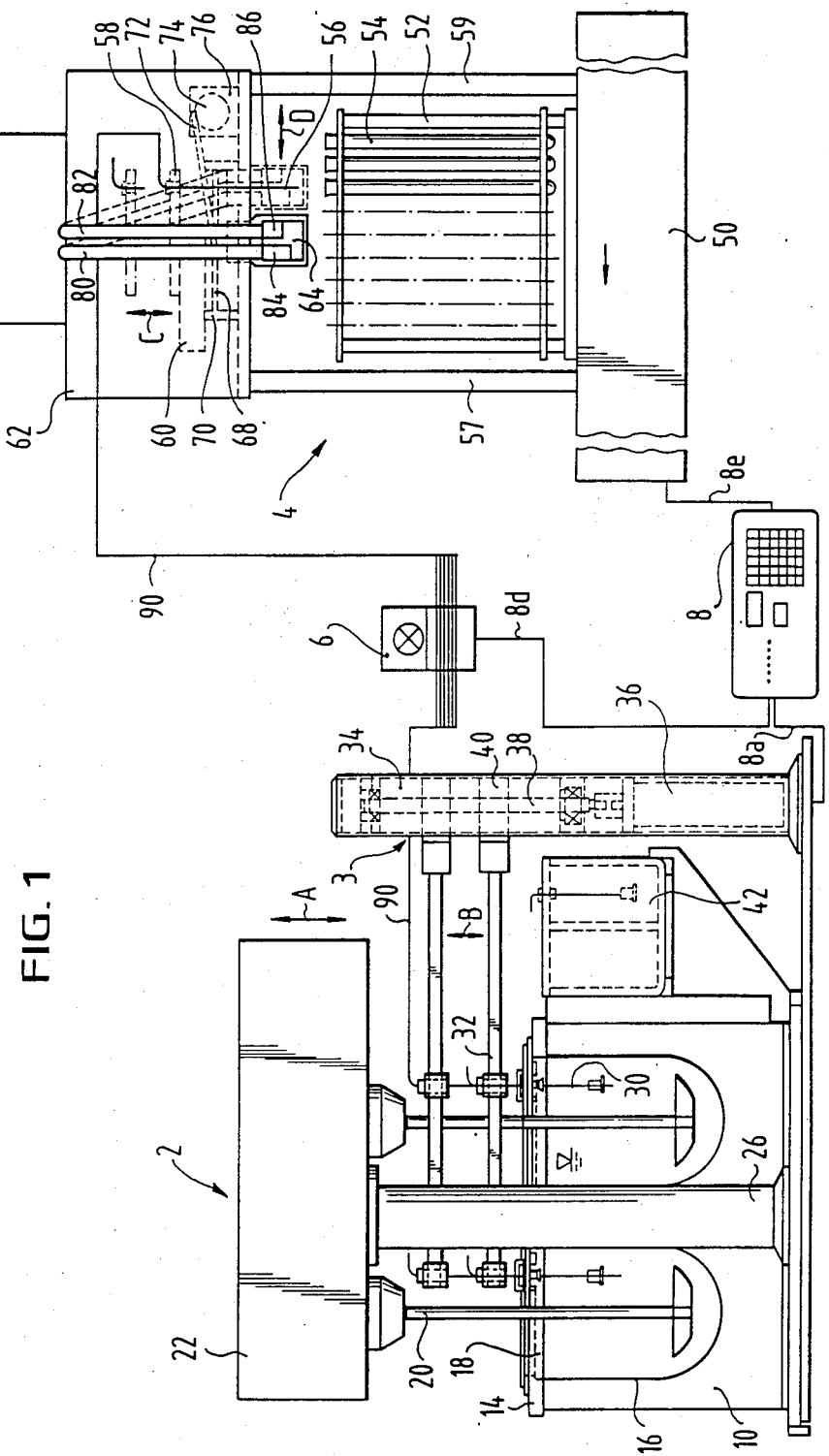
FIG. 1 is a partly schematic, partly sectional side view of a first embodiment of the sample handling apparatus of the present invention.
Figure 2:
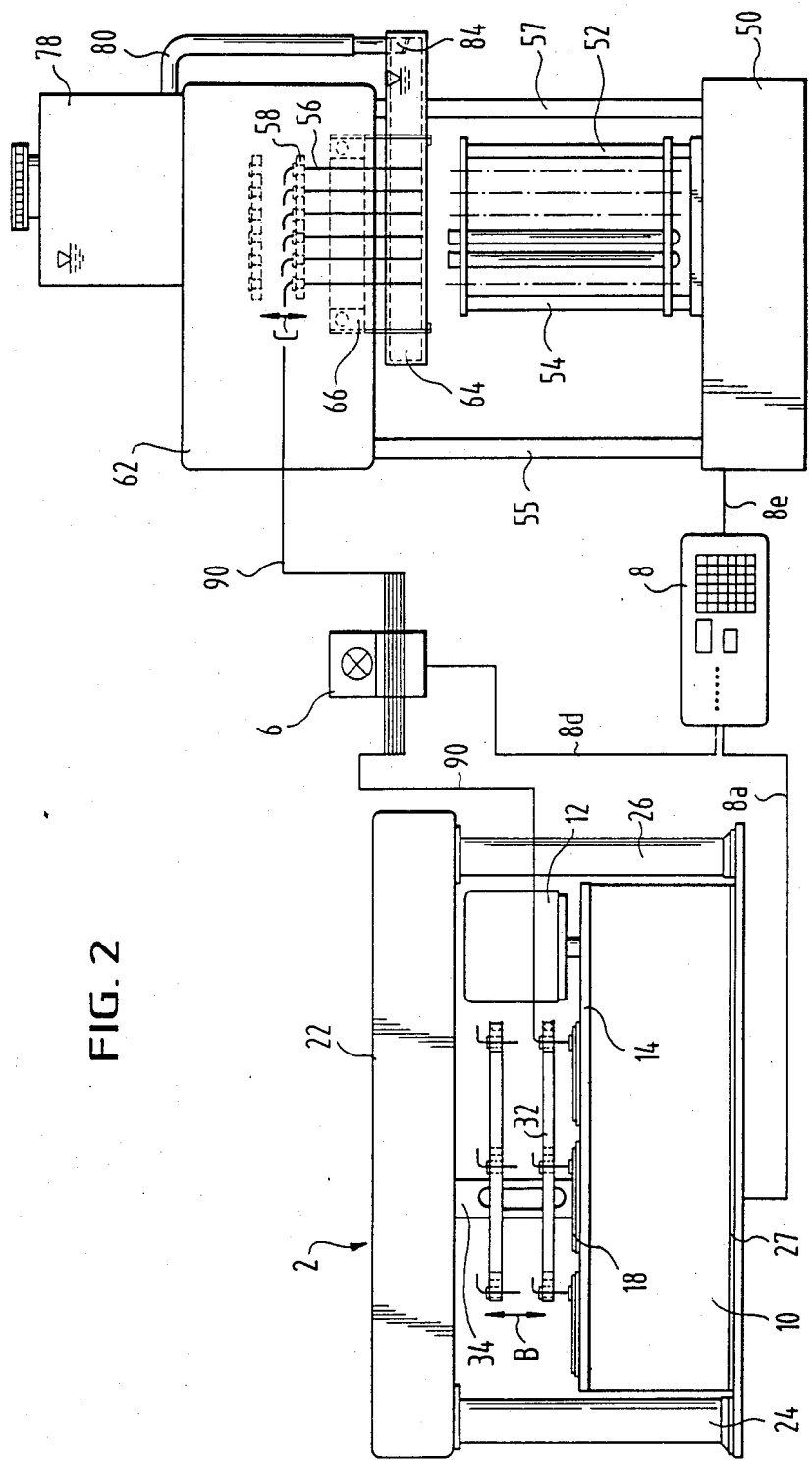
FIG. 2 is a further side view of the sample handling apparatus of FIG. 1.

As can be seen in FIGS. 1 and 2 the sample handling apparatus comprises a reaction unit 2, a sampling unit 3, a sample collecting unit 4, a six-channel hose pump 6 (in the case of six lines extending from six reaction vessels), and a control unit 8. The control unit 8 is connected to the reaction unit 2 and the sampling unit 3 by line 8a, to the sample collecting unit by line 8e and to the hose pump 6 by line 8d, to give the required control signals to the respective units.

A water reservoir 10 with a thermostat 12 is provided in the reaction unit 2. Six reaction vessels 16 are suspended in a cover plate 14 of the water reservoir 10, the reaction vessels being closed by caps 18. Agitators 20 supported in a housing 22 which also contains driving means for the agitators, extend into the reaction vessels 16. The housing 22 is mounted on a base plate 27 on top of two telescopic columns 24, 26 and the housing 22 is, thereby, movable in upward and downward direction as indicated by double arrow A in FIG. 1.

For taking samples from the reaction vessels 16 the sampling unit 3 comprises probes 30 which are arranged on a frame 32. The frame 32 is movable upwards and downwards along a column 34, as can be seen from double arrow B in FIG. 1. The frame 32 is shown in FIGS. 1 and 2 in both its lower end position as well as in its upper end position. The movement of the frame 32 is effected by a motor 36 driving a screw 38 on which screw the frame 32 is supported by means of a nut 40.

The reaction unit 2 also includes a waste receptacle 42 at the side of the water reservoir 10. The probes 30 may be placed in the waste receptacle for example for rinsing purposes.

The sample collecting unit 4 has a basic housing 50 within which a drive means (not shown) is arranged for a stand 52 carrying test tubes 54 to be filled with liquid sampled. In the example shown there is a plurality of rows of six test tubes arranged on the stand 52, and the stand 52 is moved by one row after each sample-taking operation.

A further housing 62 is mounted on columns 55, 57, 59 on top of the basic housing 50. Small pipes 56, in this embodiment six pipes, are suspended in the housing 62 above the test tubes 54 of one row. The pipes 56 are connected to the probes 30 in the sampling unit 2 through six hose lines 90 which are shown schematically in the figures. The pipes 56 are fixed in a fixture 58 which may be moved upwards and downwards by means of a motor 60, as is indicated by double arrow C in FIG. 1. The fixture 58 can be seen in FIGS. 1 and 2 in its lower end position as well as in its upper end position. At the bottom side of the housing 62 carrying the pipes 56 a trough 64 is provided, which trough is movable between a position below the pipes 56 and a position to the side of the pipes. In the last-mentioned position the passage of liquid from the pipes 56 to the test tubes 54 is unrestricted, see arrow D in FIG. 1. The trough 64 is suspended in a frame 66 which, in turn, is supported on two guide rails 68 which are fixed to the housing 62 by means of holders 70. The frame 66 is connected to the driving gear 74 of a motor 76 through a crank 72. By this arrangement the motor 76 effects the reciprocating movement of the trough 64.

As there is only little space for the trough 64 between the pipes 56 and the test tubes 54, the volume of the trough 64 is comparatively small. Therefore, it is necessary to provide for refilling the trough 64 after liquid has been taken from the trough. For this purpose a storage vessel 78 is provided on the housing 62 and two hoses 80, 82 lead from the bottom of the storage vessel 78 to the trough 64. Hoses 80, 82 are fixed to two plastic tubes 84, 86 which plastic tubes are fixed to the trough 64 and extend into the trough at different depths. If the level of the liquid in the trough 64 falls below the level of the shorted tube 86, air enters the vessel 78 through the hose 82 connected to the bottom of the storage vessel 78 and a corresponding amount of liquid flows from the bottom of the storage vessel 78 through hose 80 connected thereto, into the trough 64 until both plastic tubes 84, 86 (in particular their respective ends in the trough 64) again are below the level of the liquid. Thus, the filling of the trough 64 to a particular liquid level is ensured.

The sample collecting apparatus as described above is operated a follows. Under the control of control unit 8, the stand 52 with the test tubes 54 is brought into a position in which the test tubes 54 are right below their respective pipes 56. At the same time the trough 64 is in a position in which the trough 64 does not block the passage of liquid between the pipes 56 and the test tubes 54. The probes 30 are immersed in the liquid within the reaction vessels 16. The pump 6 is operated so that liquid is extracted from the reaction vessels 16 through the probes 30, and is pumped through lines 90 to the pipes 56, whereupon the liquid is released through the pipes 56 to the test tubes 54. The amount of liquid taken from the reaction vessels 16 is defined by the number of revolutions of the motor of the pump 6. As soon as the pump has carried out the required number of revolutions the pump 6 stops and the probes 30 are taken out of the reaction vessels 16. Thereafter the pump again operates to pump liquid in the same direction as before in order to empty the lines 90 into the test tubes 54.

After this sampling operation it is necessary that exactly the same amount of liquid which has been taken as samples from the reaction vessels 16 is compensated for by replenishing liquid. Therefore, upon termination of the sampling operation the tubes 56 are moved upwards and the trough 64 is moved into the position below the pipes 56. In the next step the pipes 56 again are moved downwards so that they extend into the replenishing liquid contained in the trough 64. Thereafter, the pump 6 is actuated by the control unit 8 in such manner that it carries out the same number of rotations in reverse direction as it had carried out during the sampling operation in the forward direction so that an amount of replenishing liquid being exactly the same as the amount of liquid taken from the reaction vessels 16 during the sampling operation is refilled into the reaction vessels 16. The refilling operation also includes the emptying of the lines 90 after drawing the proper amount of replenishing liquid from the trough 64. To this end the pump 60 empties the lines 90 into the reaction vessels 16 after the pipes 56 have been removed from the trough 64. When the replenishing liquid is pumped back from the trough 64 to the reaction vessels 16, the lines from the pipes 56 to the probes 30 are completely rinsed with replenishing liquid so that measurements will be obtained from samples subsequently taken from the reaction vessels that are uncontaminated from the previous run. Poor results could otherwise be caused by residue liquid remaining in the lines from samples which had been taken previously. After the backfeed of the replenishing liquid has been completed the pipes 56 are again moved to their upper end position and the trough 64 is moved back to its rest position to the side of the pipes 56.

Thereafter the sample collecting apparatus is ready for the next sampling operation which takes place after an interval of time defined by a corresponding adjustment in the control unit 8.

Figure 3:
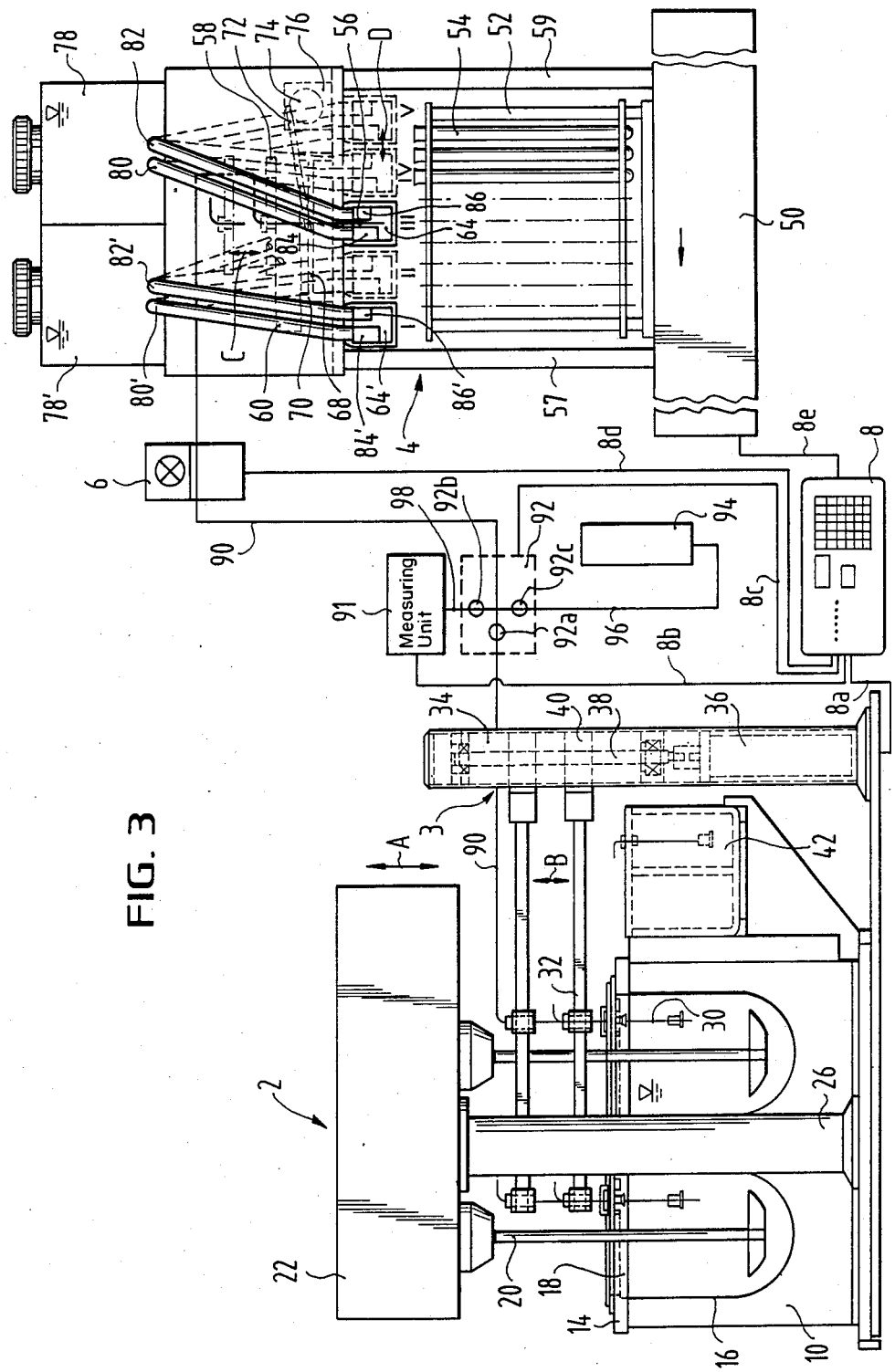
FIG. 3 is a partly schematic, partly sectional side view of the second embodiment of a sample handling apparatus.
Figure 4:
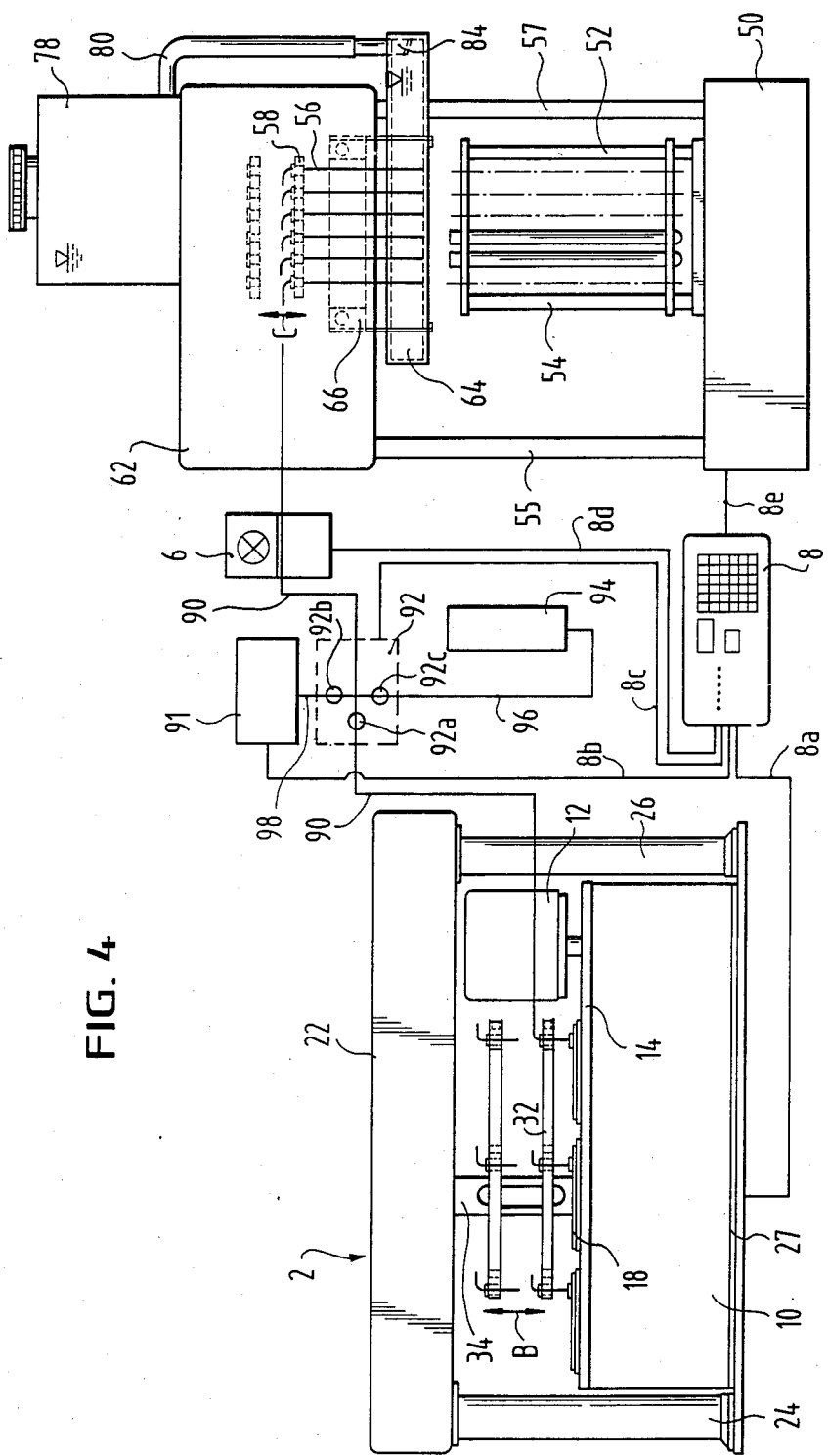
FIG. 4 is a further side view of the sample handling apparatus of FIG. 3.

The second embodiment of the present invention is shown in FIGS. 3 and 4, wherein the same reference numerals are used for the same features as in the above-described embodiment. As the second embodiment is identical to the first embodiment in many respects the identical components are not described again, but only the modifications in the second embodiment.

The second embodiment comprises, in addition to the first embodiment, an additional storage means 78' for dilution liquid, a valve means 92 having three valves 92a, 92b and 92c, a liquid container unit 94, a liquid conducting line 96 connecting the valve unit 92 to the liquid container unit 94, and a liquid conducting line 98 connecting the valve unit 92 to a measuring unit 91. The lines 96 and 98 are shown, like line 90, only schematically and in practice consist of six individual lines in case six samples are processed simultaneously. The liquid container unit 94 in practice also consists of six containers, if six samples are processed simultaneously. An additional control line 8b connects the control unit 8 to the measuring unit 91, and a further control line 8c connects the contol unit 8 to the valve unit 92 in order to control such units, respectively. The valve unit 92 is arranged on line 90 between the pump 60 and the probes 30 in order to perform the functions as described below.

The dilution liquid storage means are constructed just like the replenishing liquid storage means. In detail the dilution liquid storage means comprise a trough 64' movable in the space between the pipes 56 (in their upper position) and the test tubes 54. The trough 64' is connected to a storage vessel 78' which is provided on the housing 62 to the side of the replenishing liquid storage vessel 78. Two hoses 80', 8' lead from the bottom of the storage vessel 78' to the trough 64'. The hoses 80', 82' are fixed to two plastic tubes 84', 86' which are fixed to the trough 64' and extend into the trough 64' at different depths. By this arrangement the liquid level in the dilution liquid storage trough 64' is controlled as the liquid level in the replenishing liquid storage trough 64.

A further modification of the second embodiment is in the drive means for moving the pipes 56 up and down and in the drive means for moving the troughs 64 and 64'. The drive means for moving the pipe 56 in direction of arrow C are adapted to move the pipes 56 into a first position in which the lower ends of the pipes 56 are above the troughs 64, 64', into a second position in which the pipes 56 are immersed into the liquid of the trough 64 or 64' which is, at this moment, located below the pipes 56, and to a third position in which the pipes are immersed into the liquid contained in the test tubes 54. In order to agitate the liquid in the test tubes 54 during the dilution step the pipes 56 may be moved periodically upwards and downwards with their lower ends within the liquid in the test tubes 54 during the dilution step. For obtaining a better agitation of the liquid during the dilution step the pipes 56 may comprise, at their lower ends, agitating means like paddels (not shown). The drive means for moving the troughs 64 and 64' are similar to the drive means in the first embodiment, but are modified to move both troughs 64, 64' simultaneously such that the replenishing liquid trough 64 is below the pipes 56, or the dilution liquid trough 64' is below the pipes 56, or both troughs 64, 64' are at opposite sides of the pipes 56. FIG. 3 shows five positions which can be taken by trough 64 and/or trough 64'. If trough 64' is in position I, trough 64 will be in position III, i.e. below the pipes 56. If trough 64' is in position II, trough 64 is in position IV, which means that the pipes 56 are free to move downwards into the test tubes 54. If trough 64' is in position III, trough 64 is in position V, which means that trough 64' is below the pipes 56. This movement of the troughs may be effected by the same kind of motor and crank drive as described with respect to the first embodiment.

The operation of the second embodiment is as follows.

During the step of taking samples from the reaction vessels and during the step of refilling replenishing liquid to the reaction vessels, valve 92a is open and valves 92b and 92c are closed.

The taking of samples and the refilling of replenishing fluid is carried out as described above with respect to the first embodiment.

After the liquid samples have been filled into the test tubes 54 such liquid samples are to be diluted. To this end the dilution liquid storage trough 64' is moved into position III, the pipes 56 are immersed into the dilution liquid, valves 92a and 92b are closed and valve 92c is opened, and pump 6 is operated in clockwise direction to feed the dilution liquid from the trough 64' to the containers in the container unit 94. After an appropriate amount of dilution liquid has been drawn by the pump, the pipes 56 are removed from the trough 64', the trough 64' is moved to position II, the pipes 56 are moved down into the test tubes, and the pump 6 is operated in counterclockwise direction to draw the dilution liquid from the container unit 94 and feed this dilution liquid into the test tubes 54. During this dilution step the tubes 56 are moved up and down in the test tubes 54 to agitate the liquid therein.

Next, the diluted samples contained in the test tubes are to be fed to the measuring unit 91 (detector or photometer). To this end valves 92a and 92c are closed and valve 92b is opened, pump 6 is driven in clockwise direction while pipes 56 are immersed in the diluted liquid sample in the test tubes 54. After the required amount of diluted sample liquid is fed to the measuring unit 91, the pump 6 stops and the tubes 56 are moved to their upper position which completes this step.

If the time between taking of samples permits, the dilution and measuring step can be carried out after each sample taking step. If the time between taking samples is too short, several or all sample taking and replenishing steps are carried out first and the dilution and measuring steps are carried out thereafter. In the latter case, the stand 52 for the test tubes is moved back to its starting position after the sample taking and replenishing steps have been carried out, and the stand 52 is then again moved step-by-step to carry out the diluting and measuring steps.

We claim:

1. A sample handling apparatus comprising:
    a sample unit having a plurality of probes for taking liquid samples from a corresponding plurality of reaction vessels of a reaction unit,
    a sample collecting unit having a plurality of pipes for releasing the liquid samples into test tubes arranged in said sample collecting unit below said pipes, as well as for taking in replenishing liquid and, for this purpose, being adapted to be immersed into replenishing liquid in a first storage means also arranged in said sample collecting unit,
    lines connecting said probes with said pipes,
    a transport means connected to said lines for transporting the liquid samples from said probes to said test tubes and for transporting the replenishing liquid from said first storage means to said reaction vessels, and
    a control means for controlling at least the operation of the sampling unit, the sample collecting unit and the transport means.

2. A sample handling apparatus according to claim 1, wherein said sample collecting unit comprises a first moving means for moving said pipes in an upward and downward direction to a first position in which they are located above said first storage means and to a second position in which they are immersed in the replenishing liquid in said first storage means, and wherein said sample collecting unit furthermore comprises a second moving means for moving said first storage means in a space between said test tubes and said pipes to a position below said pipes and to a position to the side of said pipes.

3. A sample handling apparatus according to claim 2, wherein said first storage means comprise a first storage trough connected to a first storage vessel, and wherein level control means are provided for refilling said first storage trough with replenishing liquid from said first storage vessel to keep the liquid level in said first storage trough within predetermined limits.

4. A sample handling apparatus according to claim 3, wherein said first storage vessel is a closed vessel and is mounted above said first storage trough, and wherein said level control means comprise two first conduits, first ends of which first conduits are connected to the bottom of said first storage vessel and second ends of which first conduits extend into said first storage trough to different depths whereby the liquid in said first storage trough is kept within predetermined limits.

5. A sample handling apparatus according to claim 1, wherein said first storage means comprise a first storage trough connected to a first storage vessel, and wherein level control means are provided for refilling said first storage trough with replenishing liquid from said first storage vessel to keep the liquid level in said first storage trough within predetermined limits.

6. A sample handling apparatus according to claim 5, wherein said first storage vessel is a closed vessel and is mounted above said first storage trough, and wherein said level control means comprise two first conduits, first ends of which first conduits are connected to the bottom of said first storage vessel and second ends of which first conduits extend into said first storage trough to different depths whereby the liquid in said first storage trough is kept within predetermined limits.

7. A sample handling apparatus according to claim 1, comprising
    a second storage means arranged in the sample collecting unit and adapted to contain a dilution liquid,
    a valve means arranged in said lines in a position between said transport means and said probes and having three valves actuatable to allow liquid flow
    (a) between said probes and said pipes,
    (b) between said pipes and a measuring unit connected to one of said valves, and
    (c) between said pipes and a container unit connected to another one of said valves where said pipes are also adapted to be immersed into the dilution liquid in said second storage means and also into liquid contained in said test tubes, and where said control means is adapted to control also the operation of said valve means.

8. A sample handling apparatus according to claim 7, wherein said sample collecting unit comprises a first moving means for moving said pipes in an upward and downward direction to a first position in which they are located above said first and second storage means, to a second position in which they are immersed in the replenishing liquid in said first storage means or in the dilution liquid in said second storage means, and to a third position in which they are immersed in the liquid contained in the test tubes, and wherein said sample collecting unit furthermore comprises a second moving means for moving said first and second storage means in a space between said test tubes and said pipes into a position below said pipes and to positions to one side of said pipes.

9. A sample handling apparatus according to claim 8, wherein said first and second storage means comprise a first storage trough and a second storage trough connected to a first storage vessel and a second storage vessel, respectively, and wherein level control means are provided for refilling said first storage trough with replenishing liquid from said first storage vessel and for refilling said second storage trough with dilution liquid from said second storage vessel to keep the liquid levels in said first and second storage troughs within predetermined limits.

10. A sample handling apparatus according to claim 9, wherein said first storage vessel and said second storage vessel are closed vessels and are mounted above said first storage trough and said second storage trough, respectively, and wherein said level control means comprise two first conduits and two second conduits, first ends of said first and second conduits are connected to the respective bottoms of said first and second storage vessels and second ends of said first and second conduits extend into said first and second storage troughs, respectively, to different depths whereby the liquids in said first and second storage troughs are kept within predetermined limits.

11. A sample handling apparatus according to claim 7, wherein said first and second storage means comprise a first storage trough and a second storage trough connected to first storage vessel and a second storage vessel, respectively, and wherein level control means are provided for refilling said first storage trough with replenishing liquid from said first storage vessel and for refilling said second storage trough with dilution liquid from said second storage vessel to keep the liquid levels in said first and second storage troughs within predetermined limits.

12. A sample handling apparatus according to claim 11, wherein said first storage vessel and said second storage vessel are closed vessels and are mounted above said first storage trough and said second storage trough, respectively, and wherein said level control means comprise two first conduits and two second conduits, first ends of said first and second conduits are connected to the respective bottoms of said first and second storage vessels and second ends of said first and second conduits extend into said first and second storage troughs, respectively, to different depths whereby the liquids in said first and second storage troughs are kept within predetermined limits.

* * * * *